United States Patent [19]

Patel

[11] 4,363,915
[45] Dec. 14, 1982

[54] BENZYLSULFONYL DIETHYLCARBAMYL TRIAZOLE AND USE AS A SELECTIVE HERBICIDE

[75] Inventor: Natu R. Patel, Overland Park, Kans.
[73] Assignee: Gulf Oil Corporation, Pittsburgh, Pa.
[21] Appl. No.: 245,310
[22] Filed: Mar. 19, 1981

Related U.S. Application Data

[62] Division of Ser. No. 174,975, Aug. 4, 1980, Pat. No. 4,280,831.

[51] Int. Cl.³ .................. A01N 47/38; C07D 249/12
[52] U.S. Cl. .................................................. 548/265
[58] Field of Search ............................................. 548/265

[56] References Cited

U.S. PATENT DOCUMENTS 3,308,131 3/1967 McKusick .......................... 548/265
3,952,001 4/1976 Brookes et al. .................... 548/265

*Primary Examiner*—Alton D. Rollins
*Attorney, Agent, or Firm*—Deane E. Keith; Forrest D. Stine

[57] ABSTRACT

The novel compound having the structural formula

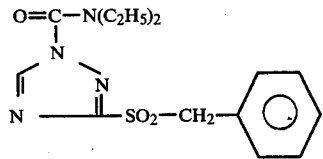

is disclosed, as well as its use by pre-emergent application to control noxious grasses and some broadleaf weeds in cool season crops such as rape, sugar beets and flax.

1 Claim, No Drawings

BENZYLSULFONYL DIETHYLCARBAMYL TRIAZOLE AND USE AS A SELECTIVE HERBICIDE

This is a division of application Ser. No. 174,975 filed Aug. 4, 1980, now U.S. Pat. No. 4,280,831.

DESCRIPTION OF THE INVENTION

Herbicides which are very effective and at the same time do not seriously injure crop plants are uncommon and are very much desired. A high degree of efficacy is desired so that application rates may be very low. In this way herbicide residues, particularly in the case of pre-emergent use, may be quickly disposed of by soil bacteria and fungi without injurious effects on the environment. Unfortunately most highly effective herbicides have very little selectivity. As the application rate is reduced to the lowest practical level, the injury to crop plants declines only slightly.

I have discovered that the compound which has the structural formula

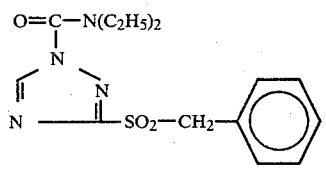

is highly effective as a pre-emergent herbicide and when applied at rates between ½ lb and 3 lb per acre it possesses useful selectivity for controlling various noxious grasses and broadleaf weeds in cool season crops such as rape, sugar beets and flax, as well as oats and barley.

Useful selectivity is particularly to be desired in pre-emergent herbicides which are employed in areas with relatively cool growing seasons. The slow rate of decomposition of herbicide residues in the soil of these areas has a tendency to cause a great deal of crop injury, so that useful selectivity is difficult to achieve.

Alkylsulfonyl carbamyltriazoles which are effective and useful as selective herbicides in warm season crops such as cotton, soybeans, maize and peanuts have been disclosed in U.S. Pat. No. 3,952,001 of Brookes et al. However, the herbicides of this reference are not directed to use in cool season crops and benzylsulfonyl compounds are not included within the scope of the disclosure.

The practice of the present invention is described and specifically illustrated in the following discussion.

SYNTHESIS OF THE HERBICIDE

A suitable method of synthesis of the novel herbicide is illustrated in the following specific procedures.

3-Benzylthio-1,2,4-triazole

A solution of 30 g (0.29 m) 3-mercapto-1,2,4-triazole in 300 ml of dry methanol containing 16.0 g (0.29 m) sodium methoxide is stirred under dry conditions, cooled to 5° C. and benzylchloride 41.3 g (0.32 m) is added dropwise. Stir the mixture at room temperature overnight, reflux 2 hours, cool and evaporate to dryness. The residue is stirred in water and the product is extracted with ethyl acetate. Dry the ethyl acetate layer and evaporate to dryness to give white product. Recrystallize from toluene-hexane, white crystals, 41.4 g (73%), m.p. 79°–80° C.

3-Benzylsulfonyl-1,2,4-triazole

To a solution of 3-benzylthio-1,2,4-triazole, 41.3 g (0.21 m) in 100 ml glacial acetic acid 65 ml of 30% hydrogen peroxide is added dropwise with stirring. The solution is gently heated to reflux and kept at reflux temperature for two hours. Then let it stir at room temperature overnight. The solution is poured into 600 ml ice water and stirred to give the product. Filter, wash with water and dry to give 42.5 g white crystals (88%) m.p. 160°–62° C.

3-Benzylsulfonyl-1-diethylcarbamoyl-1,2,4-triazole

To a solution of 3-benzylsulfonyl-1,2,4-triazole, 4.8 g (0.022 m) in 25 ml dry pyridine, 3.3 g (0.024 m) diethylcarbamoyl chloride is added dropwise. Let it stir overnight and pour into ~100 ml cold dilute hydrochloric acid. The product is extracted with ethyl acetate. Dry the organic layer and evaporate to give the desired product. Recrystallize from toluene-hexane to give white crystals, 5.8 g (81%) m.p. 87°–88° C.

The following infrared and nuclear magnetic resonance data are obtained:

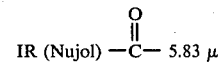

NMR (CdCl$_3$) 1.16 δ (triplet, 6H), 3.42 δ (quartet, 4H), 4.6 δ (benzylic methylene singlet, 2H), 7.25 δ (phenyl protons singlet, 5H), 8.87 δ (triazole proton singlet, 1H).

USE OF THE SELECTIVE HERBICIDE

The selective herbicide is usually applied in combination with inert carriers or diluents, as in aqueous sprays, granules and dust formulations in accordance with established practice in the art. An aqueous spray is usually prepared by mixing a wettable powder or emulsifiable concentrate formulations of a selective herbicide with a relatively large amount of water to form a dispersion.

Wettable powders comprise intimate, finely divided mixtures of selective herbicide, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the herbicidal compound comprise in each instance, a solution of the compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the herbicide is applied in formulations which desirably contain from 0.1 percent to 95 percent of the compound and from 0.1 to 75 percent of a carrier or surfactant. (Percentages are by weight.)

When a compound is to be applied to the soil, as for a pre-emergence application, granular formulations are sometimes more convenient than sprays. A typical granular formation comprises the herbicide compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

In practical tests in outdoor plots the herbicide was applied pre-emergently as an aqueous spray, made by dilution of an emulsifiable concentrate composition of the type discussed above. The spray volume was 30 gallons per acre (280.5 liters per hectare). Check plots were sprayed with the same volume of aqueous spray which contained no herbicide. The crops and weed species were planted on the same day that the soil was sprayed. Results were evaluated after 35 days. Severity of injury to plant species was evaluated on a scale of zero (no injury) to ten (total kill) and were recorded as shown below.

RESULTS OF USE OF HERBICIDE

| Application rate (1 b/A.) | Rape | Sugar beets | Flax | Alfalfa | Wheat | Oats | Barley | Cheat | Downy brome | Ryegrass | Lambsquarters | Smartweed |
|---|---|---|---|---|---|---|---|---|---|---|---|---|
| $\frac{1}{4}$ | 0 | 1 | 0 | 0 | 0.5 | 0.5 | 0.5 | 0 | 1 | 0 | 0 | 0 |
| $\frac{1}{2}$ | 0 | 0 | 0 | 0 | 1 | 0 | 1 | 2 | 5 | 3.5 | 4 | 2.5 |
| 1 | 1 | 0 | 0 | 1 | 4 | 1 | 2.5 | 3.5 | 9 | 7.5 | 8.5 | 6 |
| 2 | 4 | 2 | 1 | 5.5 | 7 | 5 | 6.5 | 9 | 10 | 10 | 9.5 | 9.5 |
| 0 (check) | 0 | 0 | 0 | 0 | 0 | 0 | 0 | 0 | 0 | 0 | 0 | 0 |

A score of 3 or less in the tabulated data indicates a rate of injury rate that can be tolerated by a crop, whereas a score of 7 or more indicates sufficient injury to a plant species to render it non-competitive. By examination of the above scores it will be seen that good control of at least three weed species was obtained at an application rate of 1 lb. per acre (1.12 kg. per hectare) and of five weeds at a 2 lb. per acre (2.24 kg. per hectare). On the other hand, at 1 lb. per acre, only one crop was injured excessively and at 2 lb. per acre sugar beets and flat were relatively uninjured. A skilled worker in the art may be guided by the above data, or may make his own outdoor tests on the weed species and specific strains of these species which infest a particular area, according to conventional practices, so as to decide upon proper application rates for specific conditions. Of the cool season crops, flax is one of the most resistant to this herbicide and can tolerate application at rates between 2 and 3 lb. per acre, where particularly good weed control is desired.

I claim:
1. 3-Benzylsulfonyl-1-diethylcarbamoyl-1,2,4-triazole.

* * * * *